(12) United States Patent
Nord et al.

(10) Patent No.: US 10,086,215 B2
(45) Date of Patent: Oct. 2, 2018

(54) METHOD AND APPARATUS PERTAINING TO TREATMENT PLANS FOR DYNAMIC RADIATION-TREATMENT PLATFORMS

(75) Inventors: Janne Nord, Espoo (FI); Olavi Pesonen, Espoo (FI); Yves Archambault, St-Jean-sur-Richelieu (CA)

(73) Assignee: Varian Medical Systems International AG, Cham (CH)

( * ) Notice: Subject to any disclaimer, the term of this patent is extended or adjusted under 35 U.S.C. 154(b) by 1666 days.

(21) Appl. No.: 13/109,541

(22) Filed: May 17, 2011

(65) Prior Publication Data

US 2012/0296148 A1 Nov. 22, 2012

(51) Int. Cl.
*A61N 5/00* (2006.01)
*A61N 5/10* (2006.01)

(52) U.S. Cl.
CPC ......... *A61N 5/1047* (2013.01); *A61N 5/1038* (2013.01)

(58) Field of Classification Search
CPC .. A61N 5/1042; A61N 5/1043; A61N 5/1047; A61N 5/1049
USPC ............................ 600/1; 378/64–65; 607/154
See application file for complete search history.

(56) References Cited

U.S. PATENT DOCUMENTS

| 7,280,633 | B2 * | 10/2007 | Cheng et al. ................... 378/65 |
| 2004/0071261 | A1 | 4/2004 | Earl et al. |
| 2004/0122311 | A1 * | 6/2004 | Cosman ........................ 600/427 |
| 2004/0247744 | A1 * | 12/2004 | Pearce ..................... A23G 3/36 426/72 |
| 2005/0123098 | A1 * | 6/2005 | Wang et al. .................... 378/65 |
| 2008/0049896 | A1 | 2/2008 | Kuduvalli |

(Continued)

FOREIGN PATENT DOCUMENTS

| CN | 1960780 A | 5/2007 |
| CN | 101983085 A | 3/2011 |

OTHER PUBLICATIONS

Cotrutz, C. et al.; "Intensity Modulated Arc Therapy (IMAT) with Centrally Blocked Rotational Fields," Physics in Medicine and Biology, vol. 45, No. 8; dated Aug. 1, 2000; pp. 2185-2206.

(Continued)

*Primary Examiner* — Christine H Matthews
*Assistant Examiner* — Joshua D Lannu
(74) *Attorney, Agent, or Firm* — Fitch, Even, Tabin & Flannery LLP

(57) ABSTRACT

A control circuit accesses patient information and treatment-platform information and uses that information to automatically suggest a treatment plan having at least one of a given number of treatment-pathway traversals wherein the given number is permitted to be greater than one and sub-treatment-pathway traversal-based physical alterations to at least one of the dynamic elements of the dynamic radiation-treatment platform. By one approach the aforementioned patient information can refer, at least in part, to the patient's external contour and a treatment target's size and position with respect to the patient. The patient information regarding the treatment target can represent the latter as a simple symmetrical geometric shape (such as a cuboid). The treatment-platform information, in turn, can refer, at least in part, to dynamic elements of the dynamic radiation-treatment platform itself.

24 Claims, 4 Drawing Sheets

(56) References Cited

U.S. PATENT DOCUMENTS

| | | | |
|---|---|---|---|
| 2008/0212737 A1* | 9/2008 | D'Souza | A61N 5/1049 378/65 |
| 2008/0317204 A1* | 12/2008 | Sumanaweera et al. | 378/65 |
| 2009/0296885 A1 | 12/2009 | Boeh et al. | |

OTHER PUBLICATIONS

Fogliata, Antonella et al.; "A Treatment Planning Study Using Non-Coplanar Static Fields and Coplanar Arcs for Whole Breast Radiotherapy of Patients with Concave Geometry," Radiotherapy and Oncology, vol. 85, No. 3; dated Oct. 29, 2007; pp. 346-354.

Palma, David A. et al.; "New Developments in Arc Radiation Therapy: A Review," Cancer Treatment Reviews, vol. 36, No. 5; dated Aug. 1, 2010; pp. 393-399.

Yu, Cedric X. et al.; "Intensity-Modulated Arc Therapy: Principles, Technologies and Clinical Implementation," Physics in Medicine and Biology, vol. 56, No. 5; dated Feb. 4, 2011; pp. R31-R54.

PCT Search Report and Written Opinion from related PCT/EP2012/059220 dated Aug. 28, 2012; 9 pages.

Chinese Office Action from related Chinese Patent Application No. 2012800234728 dated Jul. 28, 2015; 9 pages.

Chinese Office Action from related Chinese Patent Application No. 2012800234728 dated Jan. 19, 2016 with English translation; 19 pages.

Chinese Office Action from related Chinese Patent Application No. 2012800234728 dated Jul. 4, 2016 with English translation; 18 pages.

Chinese Office Action from related Chinese Patent Application No. 2012800234728 dated Jan. 11, 2017 with English translation; 6 pages.

Chinese Office Action from related Chinese Patent Application No. 2012800234728 dated May 8, 2017 with English translation; 5 pages.

Article 94(3) EPC from related European Patent Application No. 12723158.7 dated Aug. 29, 2017; 3 pages.

\* cited by examiner

METHOD AND APPARATUS PERTAINING TO TREATMENT PLANS FOR DYNAMIC RADIATION-TREATMENT PLATFORMS

TECHNICAL FIELD

This invention relates generally to radiation-treatment plans and more particularly to such plans as correspond to a dynamic radiation-treatment platform.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Radiation-treatment plans typically serve to specify any number of operating parameters as pertain to the dynamic administration of such radiation dosings with respect to a given patient. For example, many treatment plans provide for exposing the target volume to possibly varying dosages of radiation from a number of different directions.

The growing real-time flexibility of radiation-treatment platforms, however, while offering unprecedented opportunities to improve the efficacy of the planned treatment also challenges the end user with respect to properly and timely configuring that planned treatment. For example, when using an arc-therapy platform technicians sometimes find themselves challenged to quickly and correctly determine such things as an appropriate number of arcs to employ to meet the therapeutic goals of the treatment while also remaining mindful of such things as the relative positions of various objects within the treatment area (such as various parts of the treatment platform itself, the patient, the patient's couch, and so forth) to avoid in-treatment collisions.

BRIEF DESCRIPTION OF THE DRAWINGS

The above needs are at least partially met through provision of the method and apparatus pertaining to treatment plans for dynamic radiation-treatment platforms described in the following detailed description, particularly when studied in conjunction with the drawings, wherein.

Figure 1:
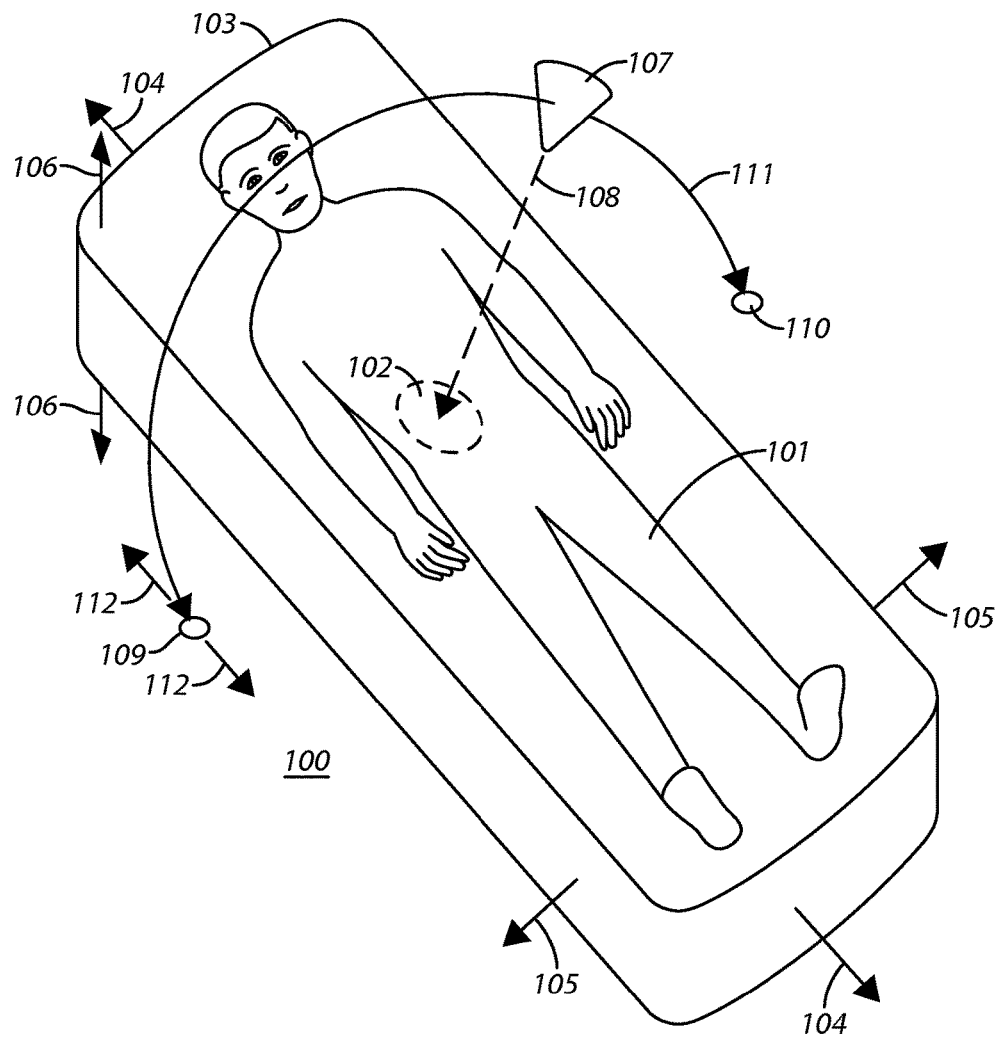
FIG. 1 comprises a perspective schematic view as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, the applicant has determined that a worthy goal in these regards is to reliably and efficiently determine a particular radiation-treatment plan for use with a dynamic radiation-treatment platform that is both efficacious and efficient (in that the plan can be executed in a least amount of time relative to other plans that might be as efficacious but that require more time to complete) while avoiding dynamic alterations that are either impossible or impractical in practice. Pursuant to these various embodiments, this can comprise accessing patient information and treatment-platform information and using that information to automatically suggest a treatment plan having at least one of a given number of treatment-pathway traversals wherein the given number is permitted to be greater than one and sub-treatment-pathway traversal-based physical alterations to at least one of the dynamic elements of the dynamic radiation-treatment platform.

By one approach the aforementioned patient information can refer, at least in part, to the patient's external contour and a treatment target's size and position with respect to the patient. If desired, the patient information regarding the treatment target can represent the latter as a simple symmetrical geometric shape (such as a cuboid). The treatment-platform information, in turn, can refer, at least in part, to dynamic elements of the dynamic radiation-treatment platform itself.

These teachings will readily accommodate application settings where the treatment-pathway traversals comprise, in whole or in part, arcs (including complete 360-degree circumnavigations). The suggested treatment plan, by one approach, can comprise, for example, a given number of treatment-pathway traversals which, in the aggregate, ensure that the treatment target receives an adequate radiation dosing during the treatment. By one approach, in combination with the foregoing or in lieu thereof, the suggested treatment plan can represent one or more sub-treatment-pathway traversal-based physical alterations to the dynamic elements of the dynamic radiation-treatment platform in order to avoid, for example, a collision between the patient and an element of that platform.

So configured, these teachings support determining an efficient, effective, and efficacious radiation-treatment plan that both accommodates and leverages the dynamic capabilities of a given dynamic radiation-treatment platform while also avoiding implementation problems that are owing to those same dynamic capabilities. This can help to ensure that an expensive radiation-treatment platform is used in an efficient manner to thereby ensure that the greatest number of patients receive a timely treatment. These teachings can be readily employed with a wide variety of dynamic radiation-treatment platforms to thereby leverage their corresponding value. These teachings are also highly scalable and can take into account as few or as many parameters of interest as may be desired.

These and other benefits may become clearer upon making a thorough review and study of the following detailed description. Referring now to the drawings, and in particular to FIG. 1, it may be helpful to first generally describe and characterize a relevant application setting. It will be understood that this example is intended to serve only in an illustrative manner and is not intended to suggest any particular limitations in these regards.

In the illustrated application setting which depicts a radiation-treatment platform 100 comprising an arc-therapy radiation treatment platform, a patient 101 having a treatment target 102 rests atop a support surface 103. Many of the elements comprising the radiation-treatment platform 100 have a dynamic characteristic. For example, the support surface 103 can move to and fro longitudinally (as represented by the arrows denoted by reference numeral 104) and back and forth laterally (as represented by the arrows denoted by reference numeral 105) as well as up and down (as represented by the arrows denoted by reference numeral 106).

As another example, a radiation source 107 capable of emitting a therapeutic radiation beam 108 can move from a first position 109 to a second position 110 by traversing a corresponding treatment pathway 111. In this illustrative example, this treatment pathway 111 comprises an arc (for the sake of simplicity this arc is shown as comprising only one-half of a complete circle; other possibilities are contemplated including arcs comprising a complete or nearly complete circle). Also in this illustrative example this treatment pathway 111 can itself be moved longitudinally (i.e., perpendicular to the direction of travel along the treatment pathway itself) as represented by the arrows denoted by reference numeral 112.

Such dynamic capabilities permit the radiation beam 108 to be directed at the treatment target 102 from a variety of different angles and in order to expose various parts of the treatment target 102 to the radiation beam 108. In a given application setting, some of this relative movement between the radiation source 107 and patient 101 can be achieved by movement of the patient 101 alone (via movement of the support surface 103), movement of the radiation source 107 alone, or by movement of both the patient 101 and the radiation source 107.

Figure 2:
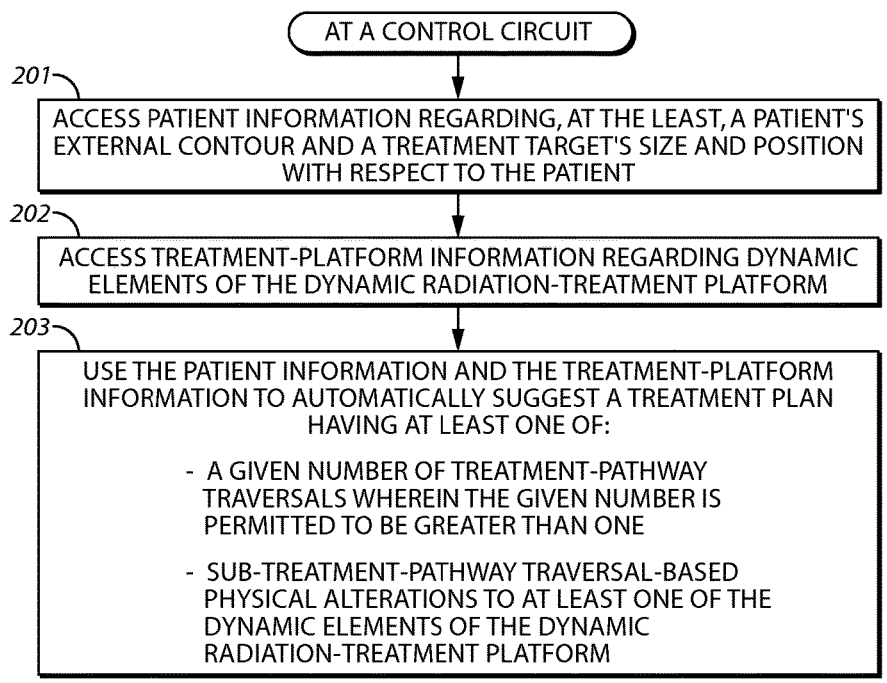
FIG. 2 comprises a flow diagram as configured in accordance with various embodiments of the invention.

Referring now to FIG. 2, an illustrative process 200 that is compatible with many of these teachings will now be presented. This process 200 can be carried out, by one approach, by a control circuit of choice. Further discussion in this regard appears further below.

At step 201, this process 200 accesses patient information regarding, at the least, a patient's external contour and the treatment target's size and position with respect to the patient. The information regarding the patient's external contour can comprise information collected at some earlier time (such as a few hours earlier that same day, or even during a previous day or week) or can comprise information that is gathered just prior to administering the radiation treatment (for example, within five, fifteen, or thirty minutes of administering the treatment). There are various known ways to obtain such metrics. Laser-based scanning comprises one such approach. Computed Tomography (CT)-based scanning comprises another such approach. As the present teachings are not particularly sensitive in these regards, further elaboration will not be provided here regarding any specific approach to making such measurements.

The information regarding the treatment target, in turn, can be obtained as well in any of a variety of ways. By one approach, for example, computed-tomography images will serve well in this regard. For many application settings this size and position information regarding the treatment target can usefully comprise three-dimensional information.

The treatment target, of course, can assume any of a variety of form factors. In fact, treatment targets such as tumors often assume a variety of irregular and non-symmetrical shapes. For the purpose of developing a specific dosing schedule these teachings will accommodate using an accurate understanding of such irregularities. That said, for the purpose of suggesting a given number of treatment-pathway traversals or for suggesting one or more specific sub-treatment-pathway traversal-based physical alterations these teachings will also accommodate using instead a simplified understanding and characterization of the treatment volume.

Figure 3:
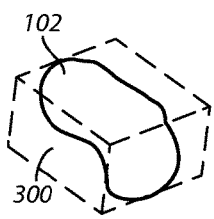
FIG. 3 comprises a perspective schematic view as configured in accordance with various embodiments of the invention.
Figure 4:
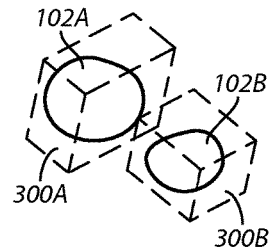
FIG. 4 comprises a perspective schematic view as configured in accordance with various embodiments of the invention.

For example, and referring momentarily to FIG. 3, the treatment target 102 can be usefully represented as a simple symmetrical geometric shape 300 such as a cuboid or other symmetrical shapes having a relatively few number of vertices. This simple shape 300 can comprise a bounding box that is sized to essentially just contain the treatment target 102 (such that portions of the treatment target 102 are tangential to various corresponding surfaces of the simple shape 300). When the treatment target comprises two or more discrete targets (such as two or more tumors), in some cases it may suffice to enclose all of these discrete targets within a single such shape. In other cases, and referring momentarily to FIG. 4, if desired, at least some of the discrete treatment targets 102A and 102B can be individually represented by corresponding simple shapes 300A and 300B, respectively. These simple shapes are considerably less computationally intensive to utilize when performing the steps described herein and at least in many application settings will yield useful results with respect to outputting helpful suggestions as per these teachings.

Referring again to FIG. 1, at step 202 this process 200 also accesses treatment-platform information regarding dynamic elements of the dynamic radiation-treatment platform. This can include, for example, information such as that noted above with respect to FIG. 1. This information can comprise (but is not limited to) metrics regarding such things as the range of available motion, speed of movement, and measurements and other characterizing information regarding the absolute location, relative location, and size of various elements of the application setting. Such information, of course, once ascertained, will tend to be relatively fixed for a given application setting and hence can likely be reused for different patients and proposed treatments.

At step 203 this process 200 then uses this patient information and this treatment-platform information to automatically suggest a radiation-treatment plan. This suggested plan, of course, pertains to use of that treatment platform to treat this particular patient using radiation therapy.

By one approach, this suggested treatment plan includes some given number of treatment-pathway traversals (wherein the given number is permitted to be greater than one). This suggestion can take into account, for example, the size and shape of the treatment target (or its corresponding surrogate bounding box as suggested above) and the specifics of the treatment platform to deliver a particular dose of radiation to a particular location to make this assessment.

Figure 5:
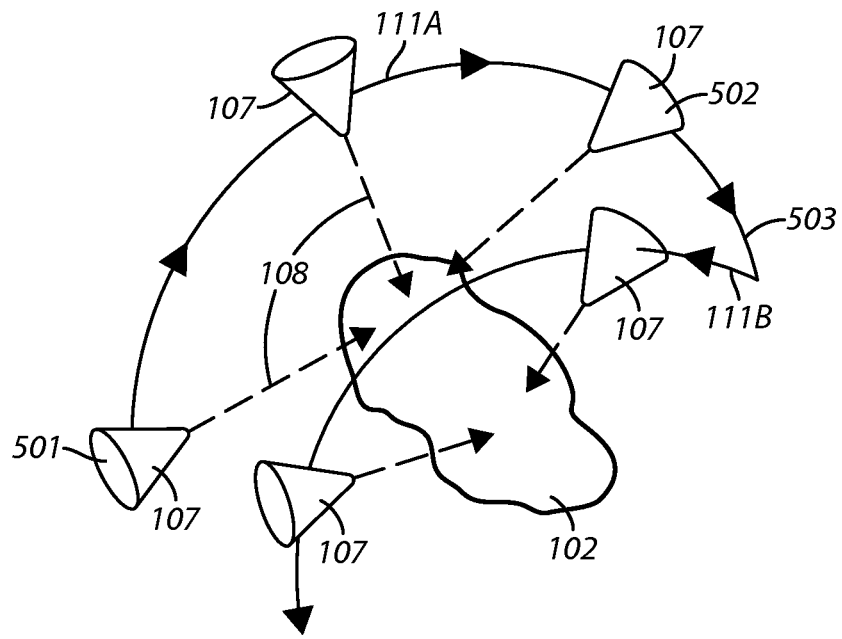
FIG. 5 comprises a perspective schematic view as configured in accordance with various embodiments of the invention.

As a simple illustrative example in these regards, and referring momentarily to FIG. 5, this step can comprise determining that only a first portion of the treatment target 102 can be suitably dosed by the radiation 108 from the radiation source 107 as the latter moves from a beginning position 501 to a concluding position 502 along a particular treatment pathway 111A. This step can also then comprise calculating a relative perpendicular movement 503 to offset the treatment pathway from its initial location and then again dosing a different portion of the treatment target 102 as the radiation source 107 moves along the offset treatment pathway 111B (the radiation source 107 this time, in this example, moving in an opposite direction along that pathway 111B).

The particular calculations undertaken pursuant to this step can seek, for example, to avoid either unduly over-exposing some part of the treatment target to multiple radiation doses or under-exposing some part of the treatment target by placing the treatment pathways too far apart from one another. As alluded to above, this step can comprise either or both of suggesting a particular given number of treatment-pathway traversals (to ensure that the treatment target receives an adequate radiation dosing during the treatment) and suggesting a particular direction of travel when traversing the treatment pathway. This step can also comprise offering specific instructions regarding how relative offsets between the treatment target/patient and the radiation source are to be achieved. This can include, for example, specific instructions regarding which element is moved, in what direction, and by how far. This may also comprise specifying a particular speed of movement as desired.

Referring again to FIG. 1, this step can also comprise, in lieu of the foregoing or in combination therewith, suggesting a treatment plan having sub-treatment-pathway traversal-based physical alterations to at least one of the dynamic elements of the dynamic radiation-treatment platform. This might comprise, for example, providing for a same kind of relative offset as between the radiation source and the treatment target as was described above where that offset occurs, however, before the radiation source has fully traversed the treatment pathway.

Figure 6:
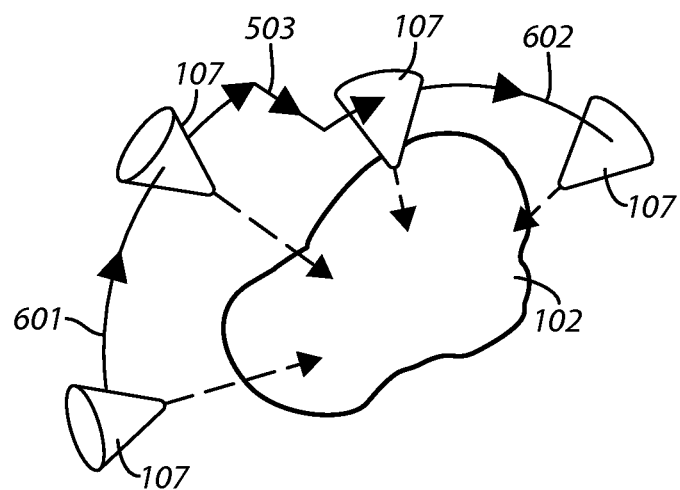
FIG. 6 comprises a perspective schematic view as configured in accordance with various embodiments of the invention.

FIG. 6 provides an illustrative example in these regards. As before, the specifics of this example are not to be taken as suggesting any limitations in these regards. In fact, it is fully anticipated and expected that this particular approach can be carried out in a great number of different ways.

In this specific example, the radiation source 107 directs its radiation beam 108 at the treatment target 102 while traversing a first sub-treatment pathway 601. Before completing the entire arc, the radiation source 107 is again perpendicularly offset by an amount denoted by reference numeral 503 and resumes (or continues, as the case may be) treating the treatment target 102 with radiation while now continuing along the remainder 602 of the treatment pathway. As before, these teachings will accommodate a variety of ways to achieve the described offset including moving the patient (for example, by moving the previously described support surface), moving the radiation source, or moving both the patient and the radiation source.

There are various reasons why is may be useful to effect such a shift prior to the radiation source having completed a complete traversal of a given treatment pathway. As one example, this may be a suitable way to accommodate a treatment target having an unusual shape or an application setting where the patient has a plurality of discrete treatment targets. As another example, this may be a suitable way to ensure avoiding a collision between the patient and an element of the dynamic radiation-treatment platform.

Those skilled in the art may be surprised to learn that the foregoing steps can be carried out in many cases without using iterative optimization techniques and without evaluating alternatives using an objective function that would, for example, map a treatment plan alternative to a single number (such that the numbers representing different alternatives could be compared to identify a best alternative). For example, a specific combination of patient and target outline information can be compared against threshold values for a set of template solutions. By one approach, these template solutions can have a predefined order of preference. For example, a single continuous trajectory can be favored in opposition to multiple discontinuous trajectories. As another example, a solution that avoids patient movements can be preferred as versus a solution that requires patient moves. If desired, a case can be classified to be the best (first) solution that passes the corresponding threshold criteria. The template solution may then be refined to better match the exact dimensions of this case. By way of illustration in these regards, fitting one or more collimators to the target comprises one example of refining such a solution.

Figure 7:
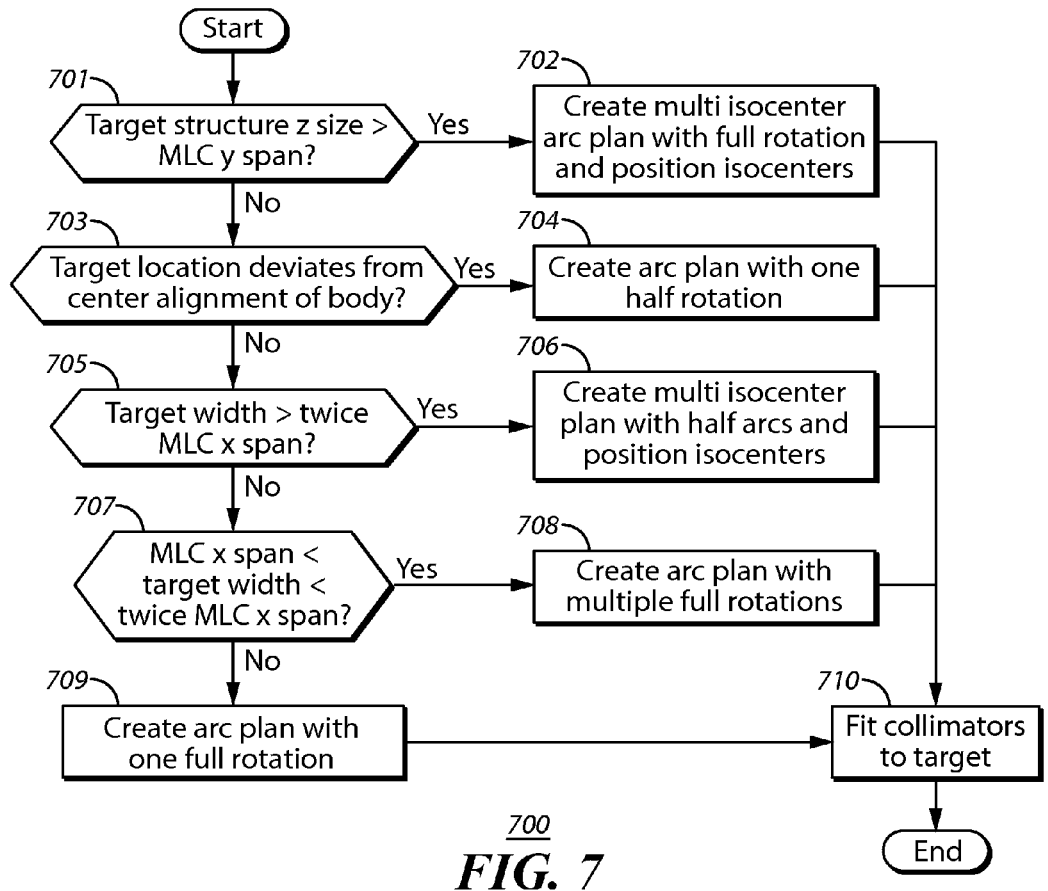
FIG. 7 comprises a flow diagram as configured in accordance with various embodiments of the invention.

As noted above, these teachings are highly flexible and can be carried out in a variety of ways. FIG. 7 depicts a more-specific example in these regards. As with other examples provided here, the specific details of FIG. 7 should not be taken as suggestions of any limitations in these regards. In fact, to a large extent, FIG. 7 is offered to instantiate that these teachings are flexible and readily applied to a variety of application settings.

At step 701, this process 700 determines whether the treatment target's structure has a height (i.e., from feet to head of the corresponding patient) Z that exceeds a length Y of a multi-leaf collimator (MLC) as comprises a dynamic element of the radiation-treatment platform, where that length Y represent a direction that is perpendicular to the direction of travel for the leaves of that multi-leaf collimator. When true, this process 700 can respond with step 702 to create a multi-isocenter arc plan (using multiple arc-shaped treatment pathways) using, for example, full rotation and position isocenters.

When step 701 is not true, at step 703 the process 700 determines whether the treatment target's location deviates with respect to central alignment of the patient's body. When true, this may lead to collision possibilities and the process 700 can respond at step 704 by creating an arc-traversal plan that includes a one-half rotation (i.e., a less-than-complete arc traversal) designed to avoid any such collision.

When step 703 is not true, at step 705 this process 700 determines whether the treatment target's width exceeds a distance that equals twice the multi-leaf collimator's X span (which corresponds to the direction in which the leaves of the multi-leaf collimator move). In such a case this process 700 responds with step 706 to create a multi-isocenter plan (having a plurality of pathway traversals) as well as half arcs and position isocenters.

When step 705 is not true, at step 707 this process 700 determines whether the X span of the multi-leaf collimator is less than the width of the treatment target, and also that the treatment target's width is less than twice this X span. When true, this process 708 responds at step 708 by creating an arc plan that employs multiple (such as 2, 5, 10, or the like) full rotations of the radiation source with respect to the treatment target. Otherwise this process 700 provides at step 709 for creating an arc plan having only a single full rotation.

Following the previously described steps 702, 704, 706, 708, and 709 this process 700 then provides for step 710 where the multi-leaf collimator is fit to the treatment target and the process 700 can conclude.

Figure 8:
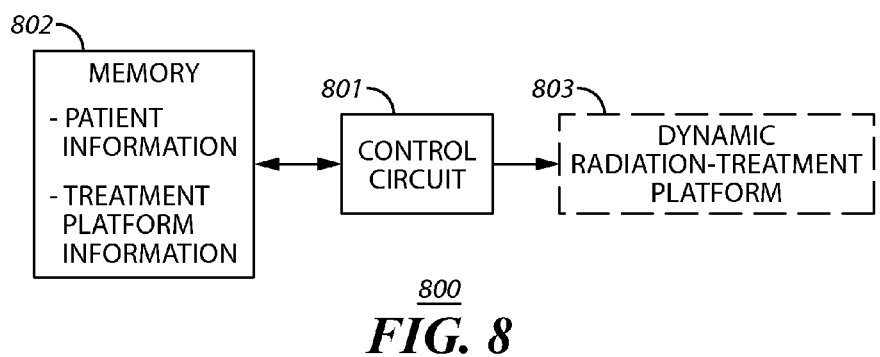
FIG. 8 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 8, an illustrative approach to such a platform 800 will now be provided.

In this example the platform 800 comprises a control circuit 801 that operably couples to a tangible digital memory 802. Such a control circuit 801 can comprise a fixed-purpose hard-wired platform or can comprise a partially or wholly programmable platform. All of these architectural options are well known and understood in the art and require no further description here. When the control circuit 801 comprises a partially or wholly programmable platform, the control circuit 801 can be programmed to carry out one or more of the steps, actions, or functions described herein. The computer instructions comprising such programming can, in turn, be stored within the control circuit 801 or within the aforementioned memory 802 as desired.

The memory 802 serves to store the aforementioned patient information and treatment-platform information. So configured, the control circuit 801 can readily access the memory 802 to avail itself of that content as per these teachings. This memory 802 can comprise a single component as suggested by the illustration or can comprise a plurality of discrete storage components. It will also be understood that part or all of this memory can be local with respect to the control circuit 801 (and share, for example, a common housing (not shown)) or can be remote from the control circuit 801 and accessed, for example, via one or more intervening networks (such as the Internet).

By one approach, the control circuit 801 can also operably couple to the dynamic radiation-treatment platform 803 (such as, for example, an arc-therapy radiation-treatment platform) for which the control circuit 801 makes the described suggested treatment plan. This can comprise simply providing the plan content in a way that an end user can review the plan and implement as they wish. This will also accommodate, however, providing specific operating instructions and programming to the dynamic radiation-treatment platform 803 to thereby cause the latter to conduct the treatment session in accordance with the suggested plan.

Such an apparatus 800 may be comprised of a plurality of physically distinct elements as is suggested by the illustration shown in FIG. 8. It is also possible, however, to view this illustration as comprising a logical view, in which case one or more of these elements can be enabled and realized via a shared platform.

So configured, the capabilities of a highly-flexible radiation-treatment platform can be more fully realized and leveraged in favor of effective results that are efficiently realized. These teachings can be applied in conjunction with a great variety of radiation-treatment platforms including but not limited to the arc-therapy platforms referred to herein for the sake of illustrative example.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method for use with a dynamic radiation-treatment platform, the method comprising:
   at a control circuit:
   accessing patient information regarding, at least, a patient's external contour and a treatment target's size and position with respect to the patient's body;
   accessing treatment-platform information regarding dynamic elements of the dynamic radiation-treatment platform; and
   using the patient information and the treatment-platform information to automatically suggest a treatment plan having
   sub-treatment-pathway traversal-based physical alterations to at least one of the dynamic elements of the dynamic radiation-treatment platform.

2. The method of claim 1 wherein the dynamic radiation-treatment platform comprises an arc-therapy radiation-treatment platform.

3. The method of claim 2 wherein a treatment-pathway traversal in said sub-treatment-pathway traversal-based physical alterations comprises an arc.

4. The method of claim 3 wherein a sub-treatment-pathway traversal in said treatment pathway traversal in said sub-treatment-pathway traversal-based physical alterations comprises only a portion of an arc.

5. The method of claim 1 wherein using the patient information comprises representing at least the treatment target as a simple symmetrical geometric shape.

6. The method of claim 5 wherein the geometric shape comprises a cuboid.

7. The method of claim 1 wherein using the patient information and the treatment-platform information to automatically suggest a treatment plan comprises, at least in part, determining a given number of treatment-pathway traversals to ensure that the treatment target receives an adequate radiation dosing during the treatment.

8. The method of claim 1 wherein using the patient information and the treatment-platform information to automatically suggest a treatment plan comprises, at least in part, determining at least one of the sub-treatment-pathway traversal-based physical alterations to at least one of the dynamic elements of the dynamic radiation-treatment platform in order to avoid a collision between the patient and an element of the dynamic radiation-treatment platform.

9. The method of claim 1 wherein suggesting a treatment plan further comprises suggesting a treatment plan having a given number of treatment-pathway traversals by suggesting both a particular number of treatment-pathway traversals as well as relative positions of said particular number of treatment-pathway traversals with respect to the patient.

10. The method of claim 1 wherein suggesting a treatment plan having sub-treatment-pathway traversal-based physical alterations to at least one of the dynamic elements of the dynamic radiation-treatment platform comprises suggesting moving a patient support platform during the treatment.

11. The method of claim 10 wherein suggesting moving a patient support platform during the treatment comprises moving the patient support platform while also moving a source of therapeutic radiation as a part of the dynamic radiation-treatment platform.

12. The method of claim 1 wherein using the patient information and the treatment-platform information to automatically suggest a treatment plan having sub-treatment-pathway traversal-based physical alterations to at least one of the dynamic elements of the dynamic radiation-treatment platform occurs without using iterative optimization.

13. The method of claim 1 wherein using the patient information and the treatment-platform information to automatically suggest a treatment plan having sub-treatment-pathway traversal-based physical alterations to at least one of the dynamic elements of the dynamic radiation-treatment platform occurs without evaluating alternatives using an objective function.

14. An apparatus comprising:
   a tangible memory having stored therein:
      patient information regarding, at least, a patient's external contour and a treatment target's size and position with respect to the patient's body;
      treatment-platform information regarding dynamic elements of a dynamic radiation-treatment platform; and
   a control circuit operably coupled to the tangible memory and configured to use the patient information and the treatment-platform information to automatically suggest a treatment plan having sub-treatment-pathway traversal-based physical alterations to at least one of the dynamic elements of the dynamic radiation-treatment platform.

15. The apparatus of claim 14 wherein the dynamic radiation-treatment platform comprises an arc-therapy radiation-treatment platform.

16. The apparatus of claim 15 wherein a treatment-pathway traversal in said sub-treatment-pathway traversal-based physical alterations comprises an arc.

17. The apparatus of claim 16 wherein a sub-treatment-pathway traversal in said treatment-pathway traversal in said sub-treatment-pathway traversal-based physical alterations comprises only a portion of an arc.

18. The apparatus of claim 14 wherein the control circuit is configured to use the patient information by representing at least the treatment target as a simple symmetrical geometric shape.

19. The apparatus of claim 18 wherein the geometric shape comprises a cuboid.

20. The apparatus of claim 14 wherein the control circuit is configured to use the patient information and the treatment-platform information to automatically suggest a treatment plan by, at least in part, determining a given number of treatment-pathway traversals to ensure that the treatment target receives an adequate radiation dosing during the treatment.

21. The apparatus of claim 14 wherein the control circuit is configured to use the patient information and the treatment-platform information to automatically suggest a treatment plan by, at least in part, determining at least one of the sub-treatment-pathway traversal-based physical alterations to at least one of the dynamic elements of the dynamic radiation-treatment platform in order to avoid a collision between the patient and an element of the dynamic radiation-treatment platform.

22. The apparatus of claim 14 wherein the control circuit is further configured to suggest a treatment plan having a given number of treatment-pathway traversals by suggesting both a particular number of treatment-pathway traversals as well as relative positions of said particular number of treatment-pathway traversals with respect to the patient.

23. The apparatus of claim 14 wherein the control circuit is configured to suggest a treatment plan having sub-treatment-pathway traversal-based physical alterations to at least one of the dynamic elements of the dynamic radiation-treatment platform by suggesting moving a patient support platform during the treatment.

24. The apparatus of claim 23 wherein the control circuit is configured to suggest moving a patient support platform during the treatment by suggesting moving the patient support platform while also moving a source of therapeutic radiation as a part of the dynamic radiation-treatment platform.

* * * * *